United States Patent [19]
Hellstrom

[11] Patent Number: 5,073,712
[45] Date of Patent: Dec. 17, 1991

[54] LIGHT SCANNER WEB PROFILE MEASUREMENT APPARATUS AND METHOD

[75] Inventor: Ake A. Hellstrom, Columbus, Ohio

[73] Assignee: ABB Process Automation, Inc., Columbus, Ohio

[21] Appl. No.: 683,844

[22] Filed: Apr. 11, 1991

[51] Int. Cl.5 ................... G01N 21/35; G01N 21/86
[52] U.S. Cl. .................. 250/252.1; 356/431; 250/341
[58] Field of Search ............... 290/252.1, 563, 340, 290/341; 356/431, 430

[56] References Cited

U.S. PATENT DOCUMENTS

| | | |
|---|---|---|
| 1,509,869 | 9/1924 | Harvey . |
| 1,936,225 | 11/1933 | Broughton . |
| 2,611,974 | 9/1952 | Stratveit et al. . |
| 3,150,264 | 9/1964 | Ehlert . |
| 3,210,546 | 10/1965 | Perron . |
| 3,216,241 | 11/1965 | Hansen . |
| 3,259,022 | 7/1966 | Vietorisz . |
| 3,334,230 | 8/1967 | Shaffer . |
| 3,350,789 | 11/1967 | Davies . |
| 3,496,365 | 2/1970 | Mounce . |
| 3,666,621 | 5/1972 | Adams . |
| 3,781,117 | 12/1973 | Laycak et al. . |
| 3,825,755 | 7/1974 | Ruskin . |
| 3,835,332 | 9/1974 | Bridges ........................... 356/430 |
| 3,843,890 | 10/1974 | Anthony, Jr. et al. . |
| 3,849,004 | 11/1974 | Cofek . |
| 3,859,537 | 1/1975 | Wolf . |
| 3,970,857 | 7/1976 | Buckson ........................... 356/431 |
| 4,260,899 | 4/1981 | Baker ........................... 356/431 |
| 4,289,964 | 9/1981 | Baker . |
| 4,500,208 | 2/1985 | Sick . |
| 4,577,104 | 3/1986 | Sturm . |
| 4,766,315 | 8/1988 | Hellstrom et al. ................... 250/341 |
| 4,767,935 | 11/1989 | Anderson et al. . |
| 4,879,471 | 11/1989 | Dahlquist . |

OTHER PUBLICATIONS

Gardner, "Moisture/Basis Weight Infrared Gage for Paper", pp. 51–54, (1968).
Thode, "How Papermakers Measure Moisture . . . ", Conrol Engineering, pp. 67–73, (1964).

Primary Examiner—Edward P. Westin
Assistant Examiner—Richard Hanig
Attorney, Agent, or Firm—Killworth, Gottman, Hagan & Schaeff

[57] ABSTRACT

A method and apparatus provide for determining properties of a web of traveling sheet material by scanning light including at least selected wavelengths such as IR and/or visible wavelengths across the web of material and also across at least two calibration samples. The signals generated in response to the scanning of the calibration samples is used to calibrate the scanning operation preferably on every scan. By providing at least two calibration samples, better estimates of average calibration parameters can be made and detection of a faulty calibration sample is facilitated. The calibration samples preferably are protected by mounting them within a scanner housing in relatively close proximity to a scanning beam generator. In addition, at least two compensation samples are supported substantially adjacent the moving web of material and preferably at least one compensation sample is positioned on each side of the web. By providing two compensation samples, fault conditions or fouling of either one of the compensation samples can be readily detected and also be used to better generate an average compensation signal. Compensation is particularly advantageous in accounting for ambient operating conditions of the process being used to manufacture the moving web of material. Both the calibration and compensation samples can be encapsulated in glass or other appropriate material to maintain their defined characteristics without effecting the monitoring operations of the optical scanner.

20 Claims, 3 Drawing Sheets

_FIG. 5_

_FIG. 7_

_FIG. 6_

LIGHT SCANNER WEB PROFILE MEASUREMENT APPARATUS AND METHOD

BACKGROUND OF THE INVENTION

The present invention relates generally to monitoring the production of a web of sheet material and, more particularly, to a method and apparatus for optically scanning a traveling web of sheet material during manufacture to determine properties of the web which are sensitive to infrared radiation (IR) and visible light wherein calibration and preferably compensation for ambient operating conditions are performed as an integral part of the scanning operation. The term "light" will be used generally herein to refer to IR and any other electromagnetic radiation such as visible light which may be used to determine properties of a web of material.

In the art of making sheet material, such as paper, coated paper, plastics and the like, it is important to monitor various characteristics of the sheet material which is typically manufactured as a relatively fast moving web. To be accurate, the monitoring operations must be frequently calibrated and often should be compensated for the ambient environment of the manufacturing process. For example, moisture content of paper is an important IR sensitive characteristic which is measured during manufacture and is highly susceptible to the ambient manufacturing environment, particularly at the wet end of the process.

A popular form for monitoring webs of sheet material traveling in a direction referred to as the machine direction, is to physically move a monitoring gauge across the web in a direction referred to as the cross direction which is substantially perpendicular to the machine direction. Thus, the gauge is moved in an effectively zigzag pattern along the web of material. It is apparent that such monitoring ignores the majority of the web since only the material along the zigzag line is monitored by the traveling gauge. The amount of material which is monitored is further reduced by standard calibration procedures which are performed off web.

Thus, on a periodic basis, such as every thirty (30) minutes, the gauge is moved off the web to an air gap or a calibration sample of the sheet material being monitored. Since the characteristics of the air gap or calibration sample are known, the gauge can be recalibrated during this time. An example of such off sheet calibration where the temperature of the calibration sample is adjusted to that of the manufacturing process is disclosed in U.S. Pat. No. 3,334,230. Even for short calibration periods, it is apparent that a substantial amount of sheet material is not monitored during recalibration. Further, other ambient environment characteristics which influence the manufacturing operation, like surrounding air moisture content, vary over time and are not compensated for by such calibration procedures.

To more completely monitor traveling webs of sheet material during manufacture, optical scanning systems have been developed for the inspection of webs of sheet materials and the determination of light sensitive properties of the webs. One optical scanning system is described in U.S. Pat. No. 3,859,537 wherein a multifaceted rotating mirror scans laser light across a moving web of material. A photocell 20 is provided at one side of the moving web of material to monitor the intensity of the scanning radiation and provide an alarm when the beam power fails or falls below a minimum acceptable level.

U.S. Pat. No. 3,970,857 describes an optical scanning system wherein a photocell 20 is located on one side of a moving web of material to monitor the intensity of the scanning radiation and a standard swatch 202 of the web material is located on the opposite side of the moving web. The swatch 202 in made to include two or more areas containing defects which are considered objectionable and should be detected by the scanning system. In this way, the optical scanning system is continuously self-checking its own operation to determine when it fails to detect the defects included in the swatch 202.

Large web scanning is described in U.S. Pat. No. 4,260,899 wherein two or more scanners are positioned across a moving web of material and synchronized to fully scan the entire width of the web.

In U.S. Pat. No. 3,843,899, an optical scanning system is described wherein an autocalibrate filter is used to replace the moving web of material at the beginning of the scan. When the scanning beam passes through the autocalibrate filter, a calibration signal is generated for the following scan.

While these optical scanning systems improve over physically moving monitoring gauges across a moving web of material to be monitored, there is a need for further improvements in optical scanning systems to provide economical, reliable scanners which include improved on-line calibration and preferably also compensate for changing ambient operating conditions of the process which is producing the web of material being monitored.

SUMMARY OF THE INVENTION

This need is met by the method and apparatus of the present invention for determining light sensitive properties of a web of traveling sheet material wherein light including at least selected wavelengths is scanned across the web of material and also across at least two calibration samples. The signals generated in response to the scanning of the calibration samples is used to calibrate the scanning operation preferably on every scan. By providing at least two calibration samples, the present invention can better estimate average calibration parameters and can sense and alert an operator in the event one of the calibration samples becomes faulty. The calibration samples preferably are protected by mounting them within a scanner housing in relatively close proximity to the scanning beam generator. In this way, the calibration samples are substantially ensured a clean environment and are unlikely to become fouled. Further, the calibration signals generated from scanning the calibration samples are not influenced by the ambient conditions of the moving web manufacturing process which is spaced a distance from the scanner housing.

In addition, in accordance with the present invention at least two compensation samples are supported substantially adjacent the moving web of material and preferably at least one compensation sample is positioned on each side of the web. By providing two compensation samples, fault conditions or fouling of either one of the compensation samples can be readily detected and also be used to better generate an average compensation signal. Compensation is particularly advantageous in accounting for the ambient operating conditions of the process being used to manufacture the moving web of material. For example, if moisture is the characteristic being measured, the moisture value(s) of the compensation samples, which are known, can be compared to the moisture values determined by the optical scanning operations with the differences being used to compensate the moisture readings obtained for the moving web of material.

Both the calibration and compensation samples can be encapsulated in glass or other appropriate material to maintain their defined characteristics without effecting the monitoring operations of the optical scanner. Such samples can be universal for some varieties of web materials being produced or can be readily changeable if calibration and/or compensation samples are required for each of a number of varieties of web material to be produced.

In accordance with one aspect of the present invention, a system for determining light sensitive properties of a web of sheet material traveling in a first direction during its manufacture comprises light source means for generating light including at least selected wavelengths. Light detector means are provided for sensing light of at least the selected wavelengths and generating signals representative thereof. Scanner means are provided for receiving light from the light source means and scanning the received light through a scanning arc which includes the web and traverses the web in a direction substantially perpendicular to the first direction. Calibration sample holder means support at least two calibration samples substantially adjacent to the light scanner means and within the scanning arc. Light collector means collect light applied by the scanner means from the web and from the at least two calibration samples, and direct light collected therefrom onto the light detector means. Processor means are connected to the light detector means for receiving the signals and determining the light sensitive properties of the web of sheet material therefrom.

The system may further comprise compensation sample holder means for supporting at least two compensation samples substantially adjacent to the web and within the scanning arc, the light collector means further providing for collecting light applied by the scanner means from the at least two compensation samples and directing light collected therefrom onto the light detector means. Preferably, the compensation sample holder means supports the at least two compensation samples on opposite sides of the web. In one embodiment, the light is back scattered to the light collector means and the light is directed upon the web, the at least two calibration samples and the at least two compensation samples at an angle to avoid specular reflection of light back to the light collector means.

The scanner means may comprise a scanning motor rotated to define the scanning arc as 360°, the scanning motor rotating a scanner mirror and being monitored by encoder means for generating pulse signals representative of the rotational position of the scanner mirror. For this embodiment, the processor means is connected to receive the pulse signals for determining the position of the scanner mirror and thereby separating the signals into web characteristic signals, calibration signals and compensation signals. The scanner means preferably further comprises chopper means for chopping the light as it is received by the scanner means. Preferably the system may further comprise a scanner housing for receiving the light source means, the scanner means and the calibration sample holder means therein.

In accordance with another aspect of the present invention, a system for determining light sensitive properties of a web of sheet material traveling in a first direction during its manufacture comprises light source means for generating light including at least selected wavelengths. Light detector means are provided for sensing light of at least the selected wavelengths and generating signals representative thereof. Scanner means receive light from the light source means and scan the received light through a scanning arc which includes the web and traverses the web in a direction substantially perpendicular to the first direction. Sample holder means are provided for supporting at least two calibration samples within the scanning arc. Light collector means collect light applied by the scanner means from the web and from the at least two calibration samples, and direct light collected therefrom onto the light detector means. Processor means are connected to the light detector means for receiving the signals and determining the light sensitive properties of the web of sheet material therefrom.

The sample holder means preferably supports the at least two calibration samples substantially adjacent to the scanner means and the at least two calibration samples are encapsulated in a material which is substantially transparent to the light to maintain their calibration characteristics over time. The sample holder means may further support at least two compensation samples within the scanning arc, the light collector means further providing for collecting light applied by the scanner means from the at least two compensation samples and directing light collected therefrom onto the light detector means. The at least two compensation samples preferably are supported substantially adjacent to the web. The compensation samples also are encapsulated in a material which is substantially transparent to the light to maintain their calibration characteristics over time.

In accordance with yet another aspect of the present invention, a method for determining light sensitive properties of a web of sheet material traveling in a first direction during its manufacture comprises the steps of: generating light including at least selected wavelengths; scanning the light through a scanning arc which includes the web and traverses the web in a direction substantially perpendicular to the first direction; supporting at least two calibration samples within the scanning arc; collecting light applied by the scanning step from the web and from the at least two calibration samples; sensing collected light from the web to generate web characteristic signals representative of light sensitive properties of the web; sensing collected light from the at least two calibration samples to generate calibration signals; and, processing the calibration signals and the web characteristic signals to determine the light sensitive properties of the web of sheet material.

Preferably the at least two calibration samples are encapsulated in a material which is substantially transparent to the light to maintain their calibration characteristics over time. The light scanning is performed by a scanner and the calibration samples are supported substantially adjacent to the scanner. The step of supporting at least two calibration samples within the scanning arc further comprises supporting at least two compensation samples within the scanning arc. Like the calibration samples, the compensation samples are encapsulated in a material which is substantially transparent to the light to maintain their calibration characteristics over time. The compensation samples are supported substantially adjacent to the web of sheet material. In one embodiment, the collected light is collected after being back scattered from the web and from the at least two calibration samples and the step of scanning the light through a scanning arc is performed at an angle relative to the web of sheet material and the at least two calibration samples to avoid specular reflection of light back from the web and from the at least two calibration samples.

It is thus an object of the present invention to provide an improved method and apparatus for determining light sensitive properties of a web of traveling sheet material by optical scanning wherein at least two calibration samples are included within the scanning area for the generation of calibration signals; to provide an improved method and apparatus for determining light sensitive properties of a web of traveling sheet material by optical scanning wherein at least two compensation samples are included within the scanning area adjacent to the web for the generation of compensation signals; and, to provide an improved method and apparatus for determining light sensitive properties of a web of traveling sheet material by optical scanning wherein at least two calibration samples and at least two compensation samples are included within the scanning area for the generation of both calibration and compensation signals.

Other objects and advantages of the invention will be apparent from the following description, the accompanying drawings and the appended claims.

DETAILED DESCRIPTION OF THE INVENTION

Figure 1:
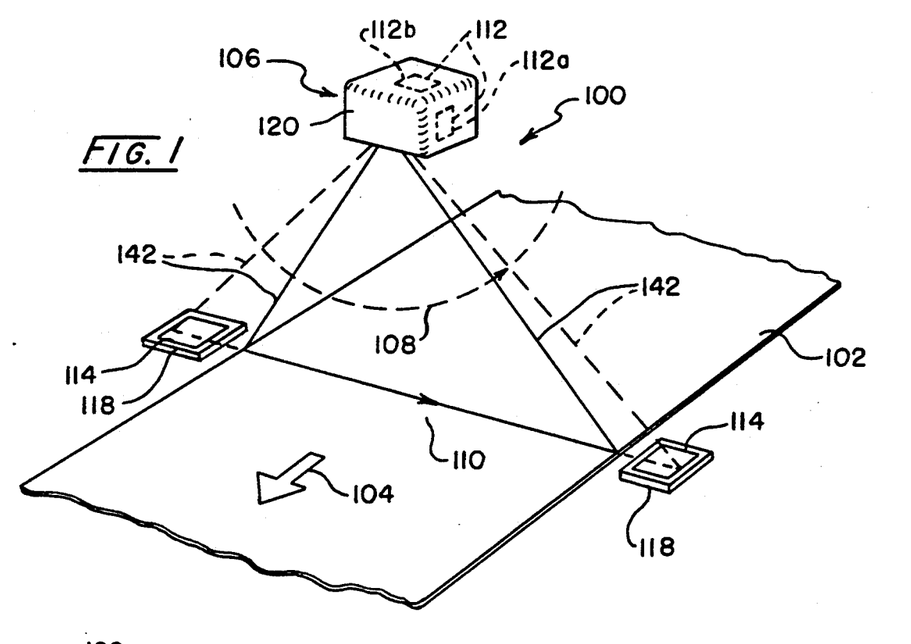
FIG. 1 is a perspective view of an optical scanning system for determining light sensitive properties of a web of material operable in accordance with the present invention.

It is initially noted that infrared radiation (IR) or visible light is currently commonly used for scanning operations for monitoring webs of material; however, the term "light" will be used generally herein to refer to electromagnetic radiation of whatever frequency which may be used now or in the future to monitor webs of material to determine properties of the webs by interaction of such electromagnetic radiation with the webs. FIG. 1 illustrates in perspective an optical scanning system 100 in accordance with the present invention for determining light sensitive properties of a web 102 of moving material as it is being manufactured. The web 102 of sheet material is traveling in a first direction indicated by the arrow 104. Scanner means comprising an optical scanner 106, best shown in FIGS. 3 and 5, scans light through a scanning arc 108 which includes the web 102 and traverses the web 102 in a direction indicated by the arrow 110 which direction is substantially perpendicular to the first direction. Sample holder means are provided for supporting at least two calibration samples 112 within the scanning arc 108.

Preferably the sample holder means also supports at least two compensation samples 114. In the illustrated embodiment, the sample holder means comprises calibration sample holder means and compensation sample holder means with the calibration sample holder means being illustrated as two channeled sample holders 116 which receive the calibration samples 112, see FIG. 3, and the compensation sample holder means being illustrated as platform sample holders 118 which receive the compensation samples 114 therein. While only two calibration samples 112 and two compensation samples 114 are shown, it is to be understood that any reasonable number of such samples as required for a given application can be provided. For example, multiple samples could be provided for multiple products to be produced.

The calibration samples 112 preferably are supported within a scanner housing 120 such that the calibration samples are supported substantially adjacent to the light scanning device in the optical scanner 106 and within the scanning arc 108. By supporting the calibration samples 112 within the housing 120 of the optical scanner 106, the calibration samples 112 are ensured a relatively clean environment which is not substantially effected by the process which is used to manufacture the web 102. The compensation samples 114, on the other hand, are positioned substantially adjacent to the web 102 such that the ambient environment of the manufacturing process effects the optical scanning of the compensation samples 114.

In this way, the characteristics of the compensation samples 114 indicated by the optical scan of the compensation samples 114 can be compared to known characteristics of the compensation samples 114 to arrive at compensation parameters which are used to compensate corresponding characteristics which are determined by scanning the web 102. In this way, errors due to the process environment can be corrected or compensated in the present invention to provide more accurate determinations of light sensitive characteristics of the web 102. The at least two compensation samples 114 are also preferably positioned with one sample on either side of the web 102 as shown in FIG. 1 such that the compensation parameters can be averaged to determine better overall compensation parameters than could be provided by a single compensation sample. Since at least two compensation samples 114 are provided in the present invention, the optical scanning of the compensation samples 114 can readily identify when one or more of the compensation samples is faulty. Since the compensation samples 114 are supported in the vicinity of the web 102, it may be preferred to provide protective air shields flowing over the compensation samples 114 to help reduce interfering contamination of the compensation samples 114 which may otherwise occur.

The two or more calibration samples 112 are selected to define appropriate characteristics for calibration of the optical scanning system 100. For example, if moisture content of a paper web is being measured, one sample may be selected to exhibit a 1% moisture content and another sample may be selected to exhibit a 20% moisture content such that two substantially end points of a typical paper moisture calibration curve are defined by the two samples and hence by the scanning operation performed on the two samples. Of course additional samples can be used to define additional points on the calibration curve or to permit calibration of additional characteristic curves for any additional characteristics to be determined by the optical scanning system 100. Since the calibration samples 112 are located substantially closer to the light scanning device of the optical scanner 106, a scaling factor is determined prior to operation of the system. It is convenient to initially place identical samples into all the sample holders 116, 118 with the scanning results of the samples in the calibration sample holders 116 being compared to the scanning results of the same samples in the compensation sample holders 118 to determine the scaling factor for each given characteristic to be monitored.

Figure 3:
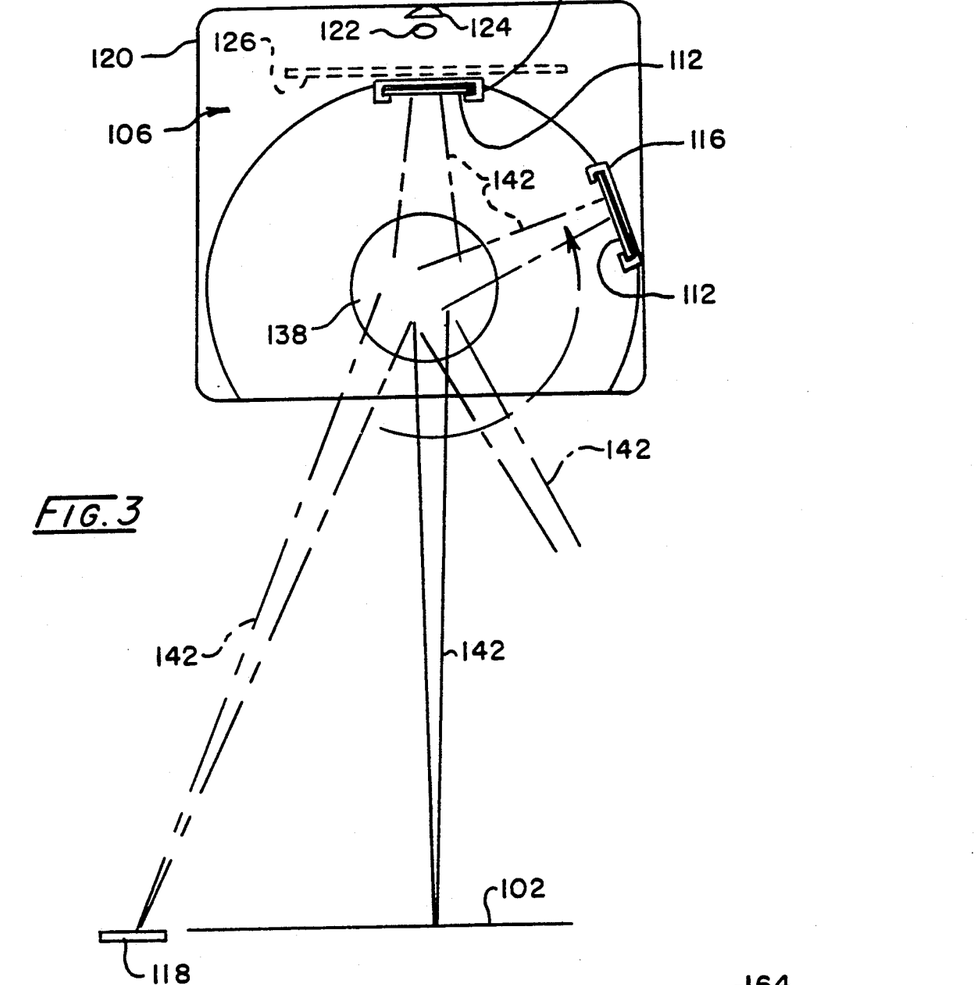
FIG. 3 is a schematic front view of a scanner/detector of the optical scanning system of FIG. 1.

The optical scanner 106 will now be described with reference to FIGS. 3 and 5. Light source means for generating light including at least selected wavelengths comprises an incandescent lamp 122 which is associated with a reflector 124. The illustrated optical scanner 106 is particularly applicable for measuring paper web profiles and more particularly moisture profiles by means of infrared radiation wavelengths generated by the incandescent lamp 122 as taught in U.S. Pat. No. 4,577,104 which is incorporated herein by reference. Accordingly, the operation of the optical scanner 106 will be described generally with reference to this application with the understanding that numerous other light scanning operations can be performed utilizing the present invention.

Light from the lamp 122 as concentrated by the reflector 124 is chopped by chopper means comprising a conventional chopper disk 126 having a plurality of notches 128 around its periphery to permit light to pass through the notches 128. The chopper disk 126, for example, may include 20 notches 128 and be rotated by a motor 130 at a rate of 60 revolutions per second to generate 1,200 light flashes per second.

Chopped light is collected by a lens system 132 and directed upon a first fixed mirror 134 which is mounted to a fixed back scatter light collection lens system 136. Light is directed from the first fixed mirror 134 to a second rotating scanner mirror 138 which is mounted for rotation by a second motor 140. The second motor 140 may be operated at an appropriate speed with speeds of from 1 to 10 revolutions per second currently appearing to be preferred for optically scanning the web 102. The rotational position of the second motor 140 and hence the scanner mirror 138 is determined by an encoder 141 which is coupled to the second motor 140 and generates a series of pulses as the motor is operated. As the scanner mirror 138 is rotated, a light beam 142 is rotated through the scanning arc 108. In the illustrated embodiment, the scanning arc 108 is 360°; however, it is apparent that a scanning mirror could be reciprocally operated to scan an appropriately smaller scanning arc which would include the web 102, the calibration samples 112 and the compensation samples 114.

As the light beam 142 is scanned across the web 102, the calibration samples 112 and the compensation samples 114, light is back scattered from these surfaces and processed. For example, the light may be processed as noted in above referenced U.S. Pat. No. 4,577,104 to determine the moisture content of the web 102. Back scattered light 144 is collected by the scanner mirror 138 and directed upon the fixed back scatter light collection lens system 136 which in turn focuses the back scattered light onto a light detector 146 which can be an integral filter/detector package 148 shown in FIG. 4 which provides for filtering the light to divide the light into selected wavelengths and for detecting the corresponding selected wavelengths of light. As best shown in FIG. 5, the light beam 142 is directed onto the web 102 and the samples 112, 114 at an angle 149 other than 90° to avoid specular reflection of light back to collector means comprising the scanner mirror 138, lens system 136 and the light detector 146.

Figure 2:
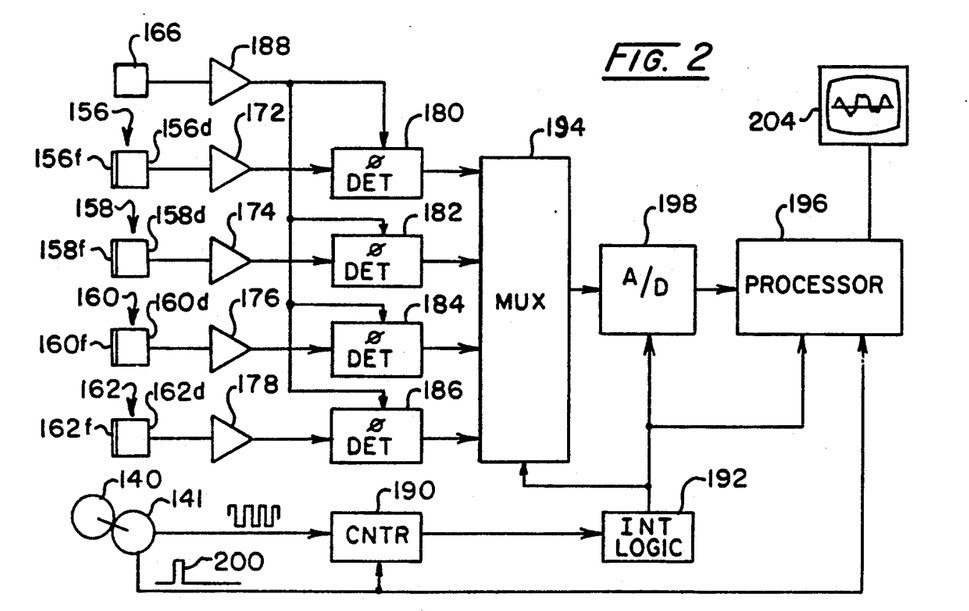
FIG. 2 is a schematic block diagram of signal processing circuitry which may be used in the optical scanning system of FIG. 1.
Figure 4:
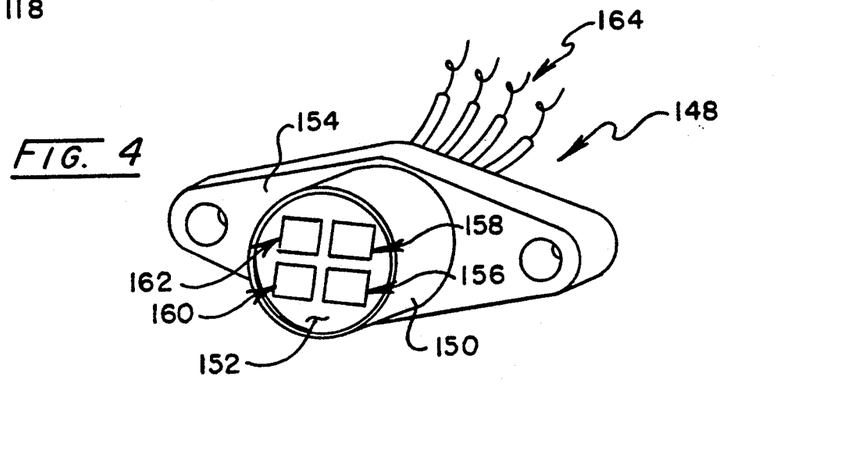
FIG. 4 is a perspective view of an integral filter/detector package which may be used in the optical scanning system of FIG. 1.

As illustrated in FIG. 4, the integral filter/detector package 148 comprises a housing 150 with an access window 152. A mounting plate 154 is provided to secure the package into the optical scanner 106. Light entering the access window 152 is simultaneously filtered and detected in a plurality of radiation channels with four radiation channels 156, 158, 160 and 162 being shown in the illustrated embodiment. To this end, light filters 156$f$, 158$f$, 160$f$ and 162$f$ and light detectors 156$d$, 158$d$, 160$d$ and 162$d$ are provided as shown in FIG. 2. Signals from the radiation channels 156, 158, 160 and 162 are transmitted via conductors 164 for processing as shown in FIG. 2. For further information regarding the integral filter/detector package 148 the reader is referred to U.S. Pat. No. 4,766,315 which is incorporated herein by reference. A separate detector 166 is provided to monitor the entire radiation of the light generated by the lamp 122 and thereby generate a phase reference signal for the circuitry of FIG. 2. It is noted that in some applications it may be desirable to include focusing lens systems 168 between the scanner mirror 138 and the calibration samples 112.

Figure 6:
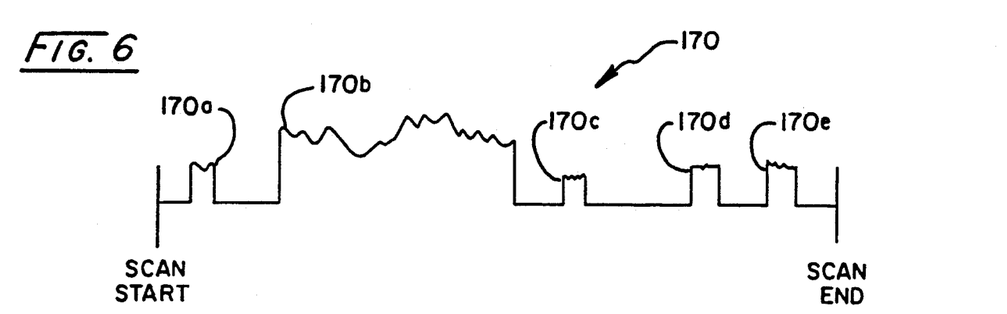
FIG. 6 is a graphical representation of a single scan of the optical scanning system of FIG. 1.

FIG. 6 is a graphical representation of a scan signal 170 for a single complete scan, 360° for the illustrated embodiment, of the optical scanning system 100. In the illustrated embodiment of the light detector 146, i.e. the integral filter/detector package 148, four such signals, one for each of the four radiation channels 156, 158, 160 and 162, are generated. The scan signal 170 comprises the following scan signal portions: a first compensation pulse 170$a$ corresponding to the scan of the compensation sample 114 on the left side of the web 102 as shown in FIG. 1; a web profile signal 170$b$ corresponding to the process raw data for the web 102; a second compensation pulse 170$c$ corresponding to the scan of the compensation sample 114 on the right side of the web 102 as shown in FIG. 1; a first calibration pulse 170$d$ corresponding to the scan of the first scanned sample 112$a$ of the calibration samples 112; and, a second calibration pulse 170$e$ corresponding to the scan of the second scanned sample 112$b$ of the calibration samples 112. The coordination and identification of these different scan signal portions is determined by the output pulses from the encoder 141.

The four signals, see the signal 170 in FIG. 6, from the radiation channels 156, 158, 160 and 162 are processed by the signal processing circuitry of FIG. 2. Each of the signals from the radiation channels 156, 158, 160 and 162 are passed to corresponding buffering input amplifiers 172, 174, 176 and 178 which in turn provide input signals for phase locked detectors, $\phi$ DET's, 180, 182, 184 and 186. The phase locked detectors 172, 174, 176 and 178 also receive a phase reference signal from the detector 166 via a buffering amplifier 188. Phase locked detectors are utilized to help maximize signal to noise and to reduce the influence of stray radiation and temperature variations as is well known in the art. For further information regarding phase locked detectors the reader is referred to above referenced U.S. Pat. No. 4,766,315.

Pulses from the encoder 141 are counted by a counter circuit 190 with defined counts being converted into data acquisition signals by interrupt logic 192. The data acquisition signals are passed to a multiplexer circuit 194 to periodically read the radiation channels 156, 158, 160 and 162 into a processor 196 via an analog-to-digital (A/D) converter 198. The processor 196 will typically be one of a large variety of commercially available microprocessors. An indexer pulse 200, one of which is generated per revolution of the motor 140, is also passed to the counter circuit 190 and the processor 196 for reset and synchronization purposes as will be apparent to those skilled in the art.

The counter 190 can be set to provide a data acquisition pulse for every X pulses from the encoder 141 which would correspond to a given angular displacement of the light beam. For example, if the encoder 141 generated 1,080 pulses per revolution of the scanner mirror 138 and data was to be taken for each one degree of movement of the light beam 142, the counter 190 is set to generate a data acquisition pulse for every three (3) encoder pulses. As is apparent, a different encoder can be used and/or different counts can be selected for reading the radiation channels 156, 158, 160 and 162 at different angular increments. Upon receiving a data acquisition pulse from the counter 190, the interrupt logic 192 steps the multiplexer 194 through the four radiation channels 156, 158, 160 and 162 such that the current analog readings or signals of the four radiation channels 156, 158, 160 and 162 are transmitted to the A/D converter 198 which converts the analog signals to digital signals for storage as raw data by the processor 196.

The processor 196 then uses the calibration pulses 170a and 170c to determine the proper calibration for interpreting the web profile signal 170b, i.e. the process raw data for the web 102, in accordance with well known calibration techniques. For example, the processor 196 can use a two-point calibration technique wherein the calibration pulses 170a and 170b define two known points on the calibration curve. The points defined by the calibration pulses 170a and 170b are known because of the known characteristics of the samples 112 which were scanned to generate the calibration pulses 170a and 170b. Thus, in its simplest form, the calibration can be performed by a two-point interpolation technique. Of course other calibration techniques will be apparent to those skilled in the art in view of the present disclosure. Preferably the processor 196 recalibrates for each scan of the scanner mirror 138; however, less frequent recalibration may be performed for given applications.

The processor 196 also uses the compensation pulses 170d and 170e to compensate, for example, for the ambient process operating conditions surrounding the web 102. For example, if moisture content is being measured and the moisture content(s) of the compensation samples 114 is know, the difference between the known moisture content(s) and the moisture content(s) indicated by the compensation pulses 170d and 170e is used to compensate the moisture content indicated by the web profile signal 170b. Since at least two compensation samples 114 are provided, an average compensation value can be readily determined.

Figures 5, 7:
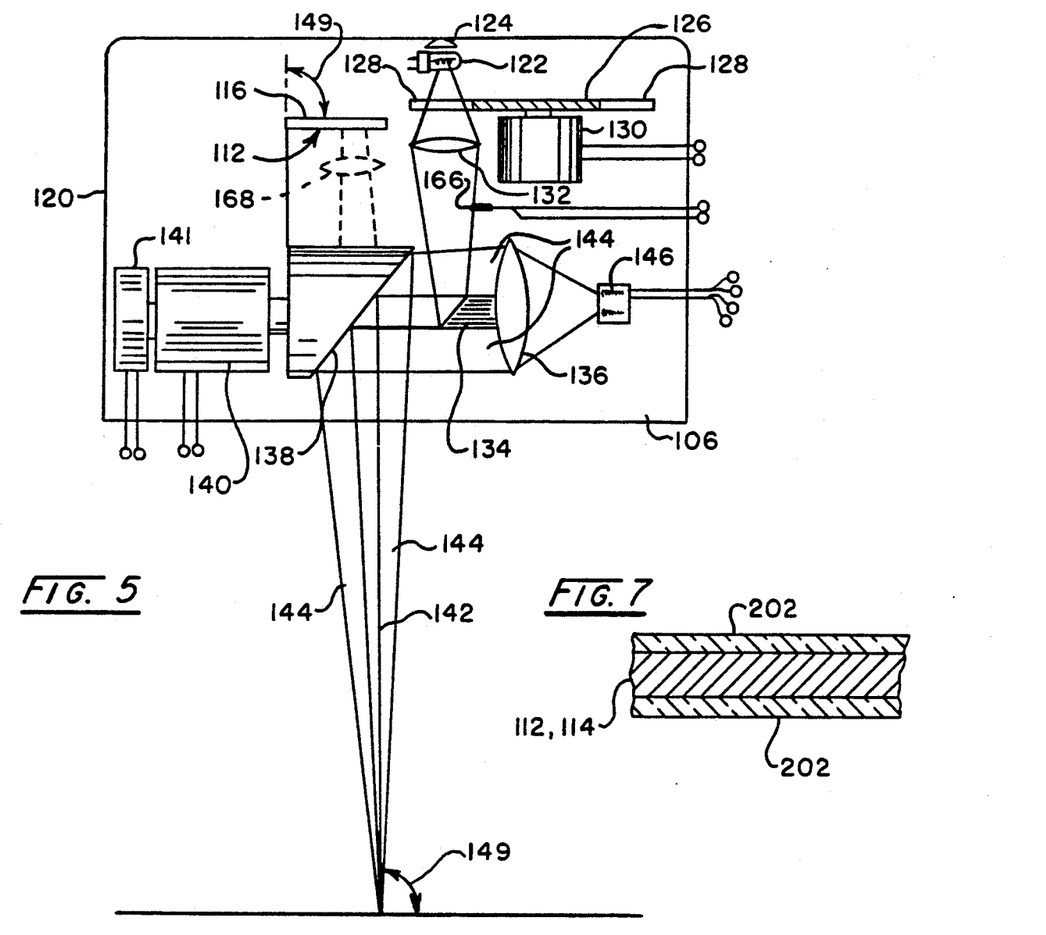
FIG. 5 is a schematic side view of the scanner/detector of the optical scanning system of FIG. 1.
FIG. 7 is a cross sectional view of a portion of a glass encapsulated paper calibration or compensation sample.

The samples 112, 114 can be stabilized, for example by encapsulation of the samples 112, 114 in glass 202 or other material which does not effect the light beam 142 being used to scan the samples 112, 114, see FIG. 7. The processor 196, if desired may ultimately display a web profile determined by the above described scanning operation by means of a cathode ray tube (CRT) display 204 as shown or other appropriate display device.

Having thus described the present invention in detail and by reference to preferred embodiments thereof, it will be apparent that modifications and variations are possible without departing from the scope of the invention defined in the appended claims.

What is claimed is:

1. A system for determining light sensitive properties of a web of sheet material traveling in a first direction during its manufacture, said system comprising:
   light source means for generating light including at least selected wavelengths;
   light detector means for sensing light of at least said selected wavelengths and generating signals representative thereof;
   scanner means for receiving light from said light source means and scanning the received light through a scanning arc which includes said web and traverses said web in a direction substantially perpendicular to said first direction;
   calibration sample holder means for supporting at least two calibration samples substantially adjacent to said light scanner means and within said scanning arc;
   light collector means for collecting light applied by said scanner means from said web and from said at least two calibration samples, and directing light collected therefrom onto said light detector means; and
   processor means connected to said light detector means for receiving said signals and determining said light sensitive properties of said web of sheet material therefrom.

2. A system for determining light sensitive properties of a web of sheet material traveling in a first direction during its manufacture as claimed in claim 1 further comprising compensation sample holder means for supporting at least two compensation samples substantially adjacent to said web and within said scanning arc, said light collector means further providing for collecting light applied by said scanner means from said at least two compensation samples and directing light collected therefrom onto said light detector means.

3. A system for determining light sensitive properties of a web of sheet material traveling in a first direction during its manufacture as claimed in claim 2 wherein said compensation sample holder means supports said at least two compensation samples on opposite sides of said web.

4. A system for determining light sensitive properties of a web of sheet material traveling in a first direction during its manufacture as claimed in claim 2 wherein said light is back scattered to said light collector means, said light being directed upon said web, said at least two calibration samples and said at least two compensation samples at an angle to avoid specular reflection of light back to said collector means therefrom.

5. A system for determining light sensitive properties of a web of sheet material traveling in a first direction during its manufacture as claimed in claim 2 wherein said scanner means comprises a scanning motor rotated to define said scanning arc as 360°, said scanning motor rotating a scanner mirror and being monitored by encoder means for generating pulse signals representative of the rotational position of said scanner mirror, said processor means being connected to receive said pulse signals for determining the position of said scanner mirror and thereby separating said signals into web characteristic signals, calibration signals and compensation signals.

6. A system for determining light sensitive properties of a web of sheet material traveling in a first direction during its manufacture as claimed in claim 5 wherein said scanner means further comprises chopper means for chopping said light as it is received by said scanner means.

7. A system for determining light sensitive properties of a web of sheet material traveling in a first direction during its manufacture as claimed in claim 1 further comprising a scanner housing for receiving said light source means, said scanner means and said calibration sample holder means therein.

8. A system for determining light sensitive properties of a web of sheet material traveling in a first direction during its manufacture, said system comprising:
   light source means for generating light including at least selected wavelengths;
   light detector means for sensing light of at least said selected wavelengths and generating signals representative thereof;
   scanner means for receiving light from said light source means and scanning the received light through a scanning arc which includes said web and traverses said web in a direction substantially perpendicular to said first direction;
   sample holder means for supporting at least two calibration samples within said scanning arc;
   light collector means for collecting light applied by said scanner means from said web and from said at least two calibration samples, and directing light collected therefrom onto said light detector means; and
   processor means connected to said light detector means for receiving said signals and determining said light sensitive properties of said web of sheet material therefrom.

9. A system for determining light sensitive properties of a web of sheet material traveling in a first direction during its manufacture as claimed in claim 8 wherein said sample holder means supports said at least two calibration samples substantially adjacent to said scanner means.

10. A system for determining light sensitive properties of a web of sheet material traveling in a first direction during its manufacture as claimed in claim 9 wherein said at least two calibration samples are encapsulated in a material which is substantially transparent to said light to maintain their calibration characteristics over time.

11. A system for determining light sensitive properties of a web of sheet material traveling in a first direction during its manufacture as claimed in claim 9 wherein said sample holder means further supports at least two compensation samples within said scanning arc, said light collector means further providing for collecting light applied by said scanner means from said at least two compensation samples and directing light collected therefrom onto said light detector means.

12. A system for determining light sensitive properties of a web of sheet material traveling in a first direction during its manufacture as claimed in claim 11 wherein said at least two compensation samples are supported substantially adjacent to said web.

13. A system for determining light sensitive properties of a web of sheet material traveling in a first direction during its manufacture as claimed in claim 12 wherein said compensation samples are encapsulated in a material which is substantially transparent to said light to maintain their calibration characteristics over time.

14. A method for determining light sensitive properties of a web of sheet material traveling in a first direction during its manufacture, said method comprising the steps of:
   generating light including at least selected wavelengths;
   scanning through a scanning arc which includes said web and traverses said web in a direction substantially perpendicular to said first direction;
   supporting at least two calibration samples within said scanning arc;
   collecting light applied by said scanning step from said web and said at least two calibration samples;
   sensing collected light from said web to generate web characteristic signals representative of light sensitive properties of said web;
   sensing collected light from said at least two calibration samples to generate calibration signals; and
   processing said calibration signals and said web characteristic signals to determine said light sensitive properties of said web of sheet material.

15. A method for determining light sensitive properties of a web of sheet material traveling in a first direction during its manufacture as claimed in claim 14 wherein said at least two calibration samples are encapsulated in a material which is substantially transparent to said light to maintain their calibration characteristics over time.

16. A method for determining light sensitive properties of a web of sheet material traveling in a first direction during its manufacture as claimed in claim 14 wherein said light scanning is performed by a scanner and said calibration samples are supported substantially adjacent to said scanner.

17. A method for determining light sensitive properties of a web of sheet material traveling in a first direction during its manufacture as claimed in claim 16 wherein the step of supporting at least two calibration samples within said scanning arc further comprises supporting at least two compensation samples within said scanning arc.

18. A method for determining light sensitive properties of a web of sheet material traveling in a first direction during its manufacture as claimed in claim 17 wherein said compensation samples are encapsulated in a material which is substantially transparent to said light to maintain their calibration characteristics over time.

19. A method for determining light sensitive properties of a web of sheet material traveling in a first direction during its manufacture as claimed in claim 17 wherein said compensation samples are supported substantially adjacent to said web of sheet material.

20. A method for determining light sensitive properties of a web of sheet material traveling in a first direction during its manufacture as claimed in claim 14 wherein said collected light is collected after being back scattered from said web and said at least two calibration samples and the step of scanning said light through a scanning arc is performed at an angle relative to said web of sheet material to avoid specular reflection of light back from said web and said at least two calibration samples.

* * * * *

UNITED STATES PATENT AND TRADEMARK OFFICE
CERTIFICATE OF CORRECTION

PATENT NO. : 5,073,712
DATED : December 17, 1991
INVENTOR(S) : Ake A. Hellstrom It is certified that error appears in the above-identified patent and that said Letters Patent is hereby corrected as shown below:

```
Col. 12, Line 14  "scanning through" should be--
                  "scanning said light through"
```

Signed and Sealed this

Fourth Day of May, 1993

Attest:

MICHAEL K. KIRK

Attesting Officer

Acting Commissioner of Patents and Trademarks